(12) United States Patent
Miccino

(10) Patent No.: US 12,739,561 B2
(45) Date of Patent: Sep. 15, 2026

(54) NOISE CANCELING SOLID STATE ELECTRONIC STETHOSCOPE WITH ADAPTED ACOUSTIC IMPEDANCE

(71) Applicant: Rodolfo Jose Miccino, Provo, UT (US)

(72) Inventor: Rodolfo Jose Miccino, Provo, UT (US)

( * ) Notice: Subject to any disclaimer, the term of this patent is extended or adjusted under 35 U.S.C. 154(b) by 259 days.

(21) Appl. No.: 18/712,532

(22) PCT Filed: Feb. 22, 2024

(86) PCT No.: PCT/US2024/016855
§ 371 (c)(1),
(2) Date: May 22, 2024

(87) PCT Pub. No.: WO2024/178200
PCT Pub. Date: Aug. 29, 2024

(65) Prior Publication Data

US 2026/0172747 A1 Jun. 18, 2026

Related U.S. Application Data

(60) Provisional application No. 63/486,604, filed on Feb. 23, 2023.

(51) Int. Cl.

| | |
|---|---|
| ***H04R 1/46*** | (2006.01) |
| ***A61B 7/04*** | (2006.01) |
| ***H04R 1/04*** | (2006.01) |
| ***H04R 17/02*** | (2006.01) |

(52) U.S. Cl.
CPC ................. *H04R 1/46* (2013.01); *A61B 7/04* (2013.01); *H04R 1/04* (2013.01); *H04R 17/025* (2013.01); *H04R 2410/03* (2013.01); *H04R 2420/07* (2013.01)

(58) Field of Classification Search
CPC .... H04R 1/04; H04R 17/025; H04R 2410/03; H04R 2420/07
USPC ............ 381/67, 338; 181/131, 135; 600/528
See application file for complete search history.

(56) References Cited

U.S. PATENT DOCUMENTS

| | | | | |
|---|---|---|---|---|
| 5,492,129 | A | 2/1996 | Greenberger | |
| 5,539,831 | A | 7/1996 | Harley | |
| 5,909,495 | A | 6/1999 | Andrea | |
| 6,498,854 | B1 | 12/2002 | Smith | |
| 7,806,226 | B2 | 10/2010 | Drummond et al. | |
| 7,991,165 | B2 | 8/2011 | Kassal et al. | |
| 8,265,291 | B2 | 9/2012 | Bridger et al. | |
| 8,275,140 | B2 * | 9/2012 | Smith | A61B 7/04 600/26 |

(Continued)

OTHER PUBLICATIONS

Yilmaz et al. "A Wearable Stethoscope for Long-Term Ambulatory Respiratory Health Monitoring," Sensors 2020, 20, 5124. Sep. 8, 2020 (Sep. 8, 2020).

*Primary Examiner* — Vivian C Chin
*Assistant Examiner* — Con P Tran
(74) *Attorney, Agent, or Firm* — Patenting Consulting Group; Roberto J Rios

(57) ABSTRACT

A solid-state electronic stethoscope with ambient noise cancellation and active noise cancellation technique. In a first embodiment, the improved signal-to-noise ratio is obtained by applying an acoustic impedance matching technique. In a second embodiment, the stethoscope further comprises an arrangement of additional sensors for active noise cancellation based on a differential acoustic signal technique.

20 Claims, 4 Drawing Sheets

(56) References Cited

U.S. PATENT DOCUMENTS

| | | | | |
|---|---|---|---|---|
| 8,396,228 | B2 * | 3/2013 | Bilan | A61B 7/04<br>381/67 |
| 9,462,994 | B2 * | 10/2016 | Rogers | A61B 5/7203 |
| 2006/0285696 | A1 | 12/2006 | Houtsma | |
| 2016/0015359 | A1 * | 1/2016 | Emmanouilidou | A61B 7/026<br>600/529 |
| 2018/0317876 | A1 | 11/2018 | Emmanouilidou et al. | |
| 2021/0345939 | A1 * | 11/2021 | Jumbe | A61B 7/04 |

* cited by examiner

NOISE CANCELING SOLID STATE ELECTRONIC STETHOSCOPE WITH ADAPTED ACOUSTIC IMPEDANCE

The present invention relates to a solid-state stethoscope showing an impedance adaptation technique for optimal capture of body sound with rejection of environmental noise and a technique that adds active noise cancellation.

For years, membrane stethoscopes with tubes that guide air to the listener's ear have remained static in their evolution. Despite the great general advance in technology, they have not experienced great advances and maintain some difficulties such as low sound intensity, acoustic interference caused by environmental noise, etc., which make interpretation of the heard sounds difficult. Likewise, given the impossibility of sharing the same sound with other doctors, it is very difficult to teach and learn the interpretation of sounds when using a conventional stethoscope.

Various devices have been designed to try to improve the acoustic quality of stethoscopes by using microphones and amplifiers to improve the intensity of the output sound, but they have always obtained poor results because they cannot avoid also increasing environmental noises along with the detected sound, thus making clinical interpretation difficult.

Conventional stethoscopes essentially have the following noise sources:

1. Environmental noise.
2. Rubbing and creaking due to operating the instrument or holding or handling the instrument.
3. Noise from rubber tubes.
4. Noises and discomfort due to pressure and rubbing of the earphones in the ear.

Furthermore, in cases of remote auscultation, with conventional electronic stethoscopes in remote locations where the doctor is far away from the patient, the doctor loses the ability to focus on a particular sound, because the device cannot mask environmental noise as its auditory system would naturally do in an in-person auscultation, thus losing the ability to perceive the subtle nuances of the auscultated sounds.

The present invention solves the problem of capturing sounds to auscultate cardiac, pulmonary, abdominal, arterial sounds and all other areas of the body that require the detection of intracorporeal sounds thanks to the great selectivity and sensitivity achieved by its acoustic and electronic impedance adaptation principle.

The problems that this invention solves are: (i) Difficulty of diagnosing due to environmental noises, lack of sensitivity and amplification of clean sound. (ii) the difficulty of sharing and training to interpret sounds; (iii) difficulty auscultating at a distance without being able to "process" external noises with the sound system.

The advantages of the stethoscope of the present invention are:

It is solid state, small in size, stable and durable.

Improves specific sensitivity to sounds through acoustic impedance adaptation, allows signal amplification as well as processing of the frequency spectrum as well as subtraction of the spectrum of unwanted sounds.

External noise rejection and noise suppression by electronic cancellation.

Noise detection and cancellation.

Signal optimization through digital processing with filters that make it similar to the traditional stethoscope but with the advantages of greater sensitivity, adaptability, increased acoustic volume, capacity for simultaneous listening by more than one operator (training, etc.) and capacity to send the sounds remotely detected using a remote consultation device.

Suitable for enhanced medical applications such as auscultation of the heart, lungs, abdomen, carotid artery.

BACKGROUND OF THE INVENTION

Several prior art documents are known, none of which describe the new features of the present invention.

U.S. Pat. No. 7,806,226B2 describes a stethoscope comprising: a sound receiving member (12) for receiving sounds, the sound receiving member being capable of transmitting the sound received by it; an earphone coupled to the sound receiving member for receiving sound transmitted by the sound receiving member; means for reducing friction noise, said means associated with the sound receiving member for reducing noise caused by relative movement between a surface and the sound receiving member of the chest piece in contact with the surface.

US20180317876A1 discloses a digital electronic stethoscope that includes an acoustic sensor assembly that uses an air-coupled electret microphone array and that includes a body sensor portion and an environmental sensor portion, the body sensor portion being configured to make contact acoustically coupled with a subject while the environmental sensor portion is configured to face outward from the body sensor portion to capture ambient noise proximate to the body sensor portion; a signal processor and a data storage system configured to communicate with the acoustic sensor assembly to receive detection signals thereof, the detection signals including an auscultation signal comprising body target sound and a noise signal; and an output device configured to communicate with the signal processor and the data storage system to provide at least one of an output signal or information derived from the output signal. The signal processor and data storage system includes a noise reduction system that eliminates both stationary noise and non-stationary noise from the detection signal to provide a clean auscultation signal substantially free of distortion. The signal processor and data storage system further include an auscultation sound classification system configured to receive the clean auscultation signal and provide a classification thereof as at least one of a normal respiratory sound or an abnormal. respiratory sound.

U.S. Pat. No. 5,909,495B1 describes a stethoscope for reducing background noise comprising a housing having a receiving part and an audio output means; the receiving part having a plurality of noise ports; a microphone isolator located within the receiver portion; a noise-cancelling microphone having a front end and a rear end enclosed by the microphone isolator; an acoustic tube having an acoustic waveguide connected to the microphone isolator for channeling an input signal; a chest piece having a sound diaphragm pickup to receive the input sound and noise signal connected to an acoustic tube to allow a pressure gradient noise port placed at the rear end of the microphone and internally behind the noise port, that is, an air coupling.

U.S. Pat. No. 6,498,854B1 discloses an air-coupled acoustic-to-electric converter transducer for detecting body sounds. The transducer comprises a capacitive sensor, whereby the diaphragm of a stethoscope forms a plate of a condenser, the second plate of the condenser being coplanar with respect to the diaphragm. The capacitance of the two plates varies with the distance between them, said distance being modified by the movement of the diaphragm in response to sound pressure. The sensor, circuitry, manufacturing methods, and improvements are described.

U.S. Pat. No. 5,492,129A describes an air-coupled noise-reducing stethoscope comprising a body sound sensor for placement on a body to detect inner body sounds and emit an electrical signal in response, an ambient noise sensor, proximate to the sound sensor body, for detecting environmental noise and outputting an electrical signal in response, and a difference comparator for accepting the electrical signals from both sensors and providing a difference signal in response, wherein the contribution of the difference signal from the environmental noise is smaller than the contribution of environmental noise to the electrical body sound sensor signal to cancel noise interference in the electrical signal of the body sound sensor.

U.S. Pat. No. 5,539,831A discloses an air-coupled active noise monitoring stethoscope that allows a doctor or paramedic to check vital signs in the presence of high levels of background noise. A digital processing technique is used to remove noise from the output of a primary detection sensor, whose impedance does not match that of the air and is therefore less sensitive to external airborne noise. Instead of a microphone, the detector uses a piezoceramic transflexural actuator mounted on a cylindrical piece of brass, with a polyurethane coating placed over the active side of the sensor to keep it waterproof and amplify the sensor's response. An identical sensor is placed on top of the device to detect background noise adjacent to the device, and the signals are combined to obtain a signal free of background noise. A third sensor is also used to electronically eliminate noise detected by the main sensor, with the third sensor being positioned to capture noise coupled through the patient's body. The time-varying voltages of the signals output by these sensors are digitized and processed by the digital signal processor, and the output is used to drive the headphone speakers. The digital signal processor uses a least mean square algorithm to digitally subtract the portion of the detector signal that is correlated with the second and third sensor signals. Additionally, the noise that penetrates the earcups of the headphones is reduced by using the speakers to generate anti-noise. Anti-noise is generated by a filtered adaptive ear sensitivity detected by a microphone inside the headphones.

SUMMARY OF THE INVENTION

A solid-state electronic noise-canceling stethoscope featuring an acoustic impedance-matched mechanism. A first embodiment comprises a solid-state electronic stethoscope that has a direct acoustic coupling path with matched acoustic impedance that provides maximum intensity transfer of the desired auscultation sounds and maximum rejection of environmental noise. The second embodiment comprises a solid-state electronic stethoscope having a direct acoustic coupling path with matched acoustic impedance with maximum rejection of ambient noise and with an additional array of sensors and circuitry for active cancellation of additional environmental noise.

BRIEF DESCRIPTION OF THE DRAWINGS

Further features and advantages of the invention will become apparent from the following detailed description taken in conjunction with the accompanying figures showing illustrative embodiments of the invention, in which:

FIGS. 4A and 4B show the circuit block diagrams of the solid state stethoscope optimal body sound pickup with environmental noise rejection with active noise cancellation.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The present invention comprises two embodiments. The first embodiment benefits from the sensitivity and ambient noise rejection obtained through a solid-state acoustic impedance matching mechanism. The second embodiment further comprises an additional sensor array for additional active cancellation of ambient noise and cancellation of handling noises, such as rubbing, creaking and other noises produced during auscultation.

Acoustic Impedance Matched Noise Canceling Solid State Electronic Stethoscope

Figure 1:
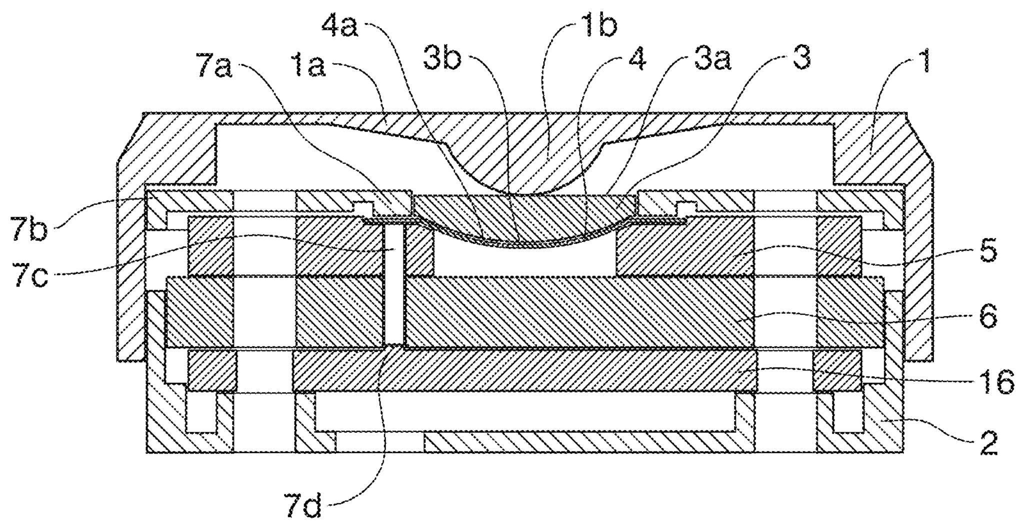
FIG. 1 shows a sectional view of the assembly and parts of the first embodiment of the stethoscope of the present invention.
Figure 1A:
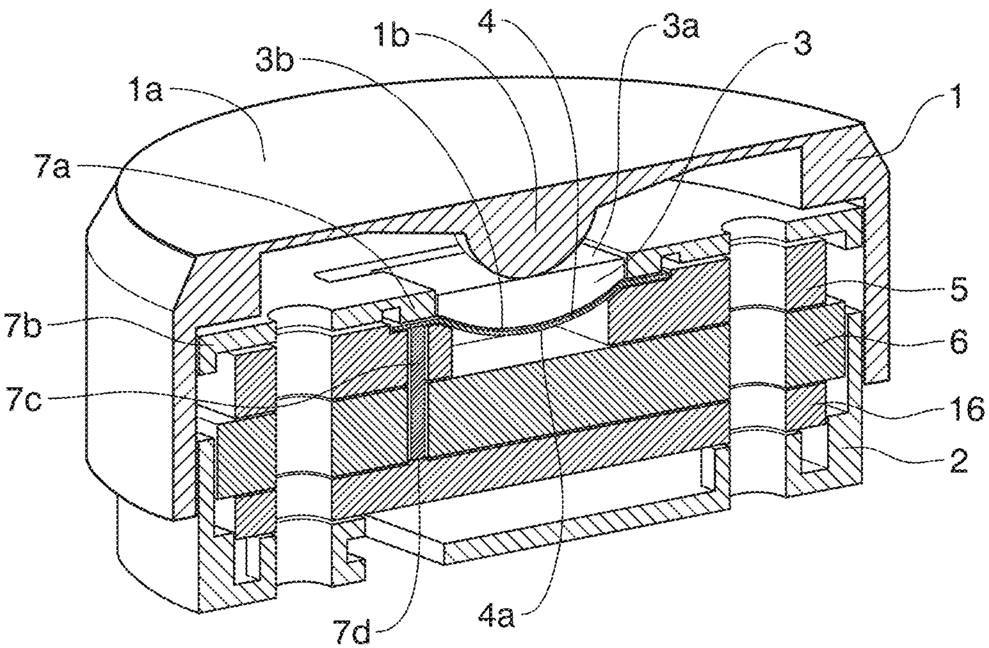
FIG. 1A shows a perspective view of the assembly and parts of the first embodiment of the stethoscope of the present invention.

FIGS. 1 and 1A show the first embodiment of the stethoscope of the present invention, comprising a solid-state direct-coupled electronic stethoscope based on an impedance-matched acoustic signal conduction mechanism to maximize the acquisition of sounds from the body with rejection of environmental noise. In this way, the acoustic waves coming from the body of the patient, being listened to, are captured and transmitted with the greatest transfer of energy to the sensors, and those sounds coming from the environment that travel through air are rejected due to the great impedance mismatch.

FIGS. 1 and 1A show a cylindrical cap 1 with a membrane 1*a* consisting of an outer circular surface that rests on the patient's skin to auscultate sounds coming from the area of interest. This membrane, which in a preferred embodiment is 38 mm in diameter, has a conical interior volume ending in a lower spherical central member 1*b* in contact with the acoustic coupler 3. The complete piece is preferably made of TPU (thermoplastic polyurethane) or silicone with similar characteristics, showing a density close to that of human tissue of 1.1 gr/cm3+-20%, that is, 0.88-1.32 gr/cm3. The material used in the cylindrical cap 1 is a biocompatible material that does not cause irritation when in contact with the skin, has great elasticity and mechanical resistance. The cylindrical cap 1 is the first link in the acoustic signal capture path and has an acoustic impedance similar to that of the human tissue. The diameter of 38 mm was chosen as it allows the best compromise of capturing acoustic vibrations versus comfort and accessibility to the various areas of the body to be auscultated. The outer membrane 1*a* of the cylindrical cap 1 has a thickness of 0.4 mm that provides resistance, as well as good coupling at low frequencies. The acoustic coupler 3 is preferably 9 mm wide by 10 mm long, it is preferably made of flexible polyurethane (Ebalta® GM951) or any material with similar characteristics, showing a density close to that of human tissue of 1.1 gr/cm3+–20% that is, 0.88-1.32 gr/cm3. The acoustic coupler 3 has a flat upper face 3*a* in contact with the lower spherical central member 1*b* of the membrane 1*a*, receiving the acoustic vibrations coming from contact with the auscultated body by direct coupling. The acoustic coupler 3 also has a density similar to that of human soft tissue and a curved lower face 3*b* directly coupled by contact to the sensor sheet 4. Sensor sheet 4 is a piezoelectric sheet preferably made of Piezo PDVF (polyvinylidene fluoride or vinylidene polyfluoride), preferably 9 mm×17 mm and 45 μm thick, with micrometallic silver electrodes, with a curved central zone 4*a* of 3 mm maximum depth and flat lateral ends, that converts into electrical impulses the acoustic vibrations thus received from the contact with the auscultated body, thus obtaining maximum acoustic transfer and rejecting the noise coming from the air as a whole. The chosen curvature of the sensor sheet 4 optimizes the propagation of acoustic waves in the direction of its long longitudinal axis, thus transmitting the vibrations received on the axis in which the piezoelectric material of the PDVF Piezo sheet has the greatest piezoelectric conversion efficiency.

The rear plate 5 acts as a support (backing) for the sensor sheet assembly 4 and for the acoustic coupler 3. The cylindrical backrest 6 has a mass of preferably 16 g of copper. The rear plate 5 and the cylindrical backrest 6 are preferably made of ABS (Acrylonitrile Butadiene Styrene) material or any material with similar characteristics, showing a density close to that of human tissue of 1.1 gr/cm3+–20%, that is, 0.88-1.32 gr/cm3. The cylindrical backrest 6 provides additional support (inertial support mass) to the assembly (backing) to achieve good response at low frequencies of the auscultated sounds, obtaining a bandwidth of about 20 Hz to 4 Khz that provides all the range necessary for diagnosis in any auscultation territory.

The upper inner conductive cover 7*b*, preferably made of flexible silicone with high electrical conductivity, provides connection to ground (GND) through the contact tab 7*a* to the upper face (pole) of the PDVF Piezo sensor sheet 4, both also acting as shielding to electronic noise and mainly to 50/60 hz electromagnetic noise coming from urban power lines. The vertical conductive connector 7*c*, also preferably made of flexible silicone with high electrical conductivity, provides electrical connection to the underside of the sensor sheet 4 of Piezo PDVF to the input contact pad 7*d* of the printed circuit board PCB 7. Finally, the lower conductive cover 2, preferably made of flexible silicone with high electrical conductivity, encapsulates the entire assembly, completing the electromagnetic shielding with inner top conductive cover 7*b*.

The speed of sound transmission in air is approximately 340 m/s, while in human soft tissue, whose approximate average density is 1.1 gr/cm3, it is approximately 1,540 m/s. For clarity enhancement, and taking into account a linear medium, the acoustic impedance (Z) can be calculated as the product of the density (D) of the medium and the speed (V) at which sound passes through it.

$$Z(\text{acoustic}) = D \times V$$

The acoustic impedance unit is measured in rayl (Ry), in Kg/(m2s). In general it varies with temperature and pressure, for example for air:

$$Z(\text{air}) = 1.225\ Kg/m^3 * 340\ m/s = 416.5\ Ry \text{ or } Kg/(m2s) \text{ at approximately @ } 15\ ^\circ\text{C and } 101.325 kPa$$

While, for human soft tissue:

$$Z(\text{Soft Tissue}) \approx 1{,}100\ Kg/m^3 * 1{,}540\ m/s = 1{,}694{,}000\ Ry \text{ or } Kg/(m2s) \text{ at approximately @ } 15\ ^\circ\text{C and } 101{,}325 kPa$$

A value of 1,100 Kg/m3 (1.1 gr/cm3) for human soft tissue is used as a simplified calculation reference. These values are approximate since they also depend on other factors such as chemical composition, hydration level, etc., and are described only for the purpose of evidencing the great difference in acoustic impedance between air and human tissue.

When an acoustic wave is transmitted from a medium with a first acoustic impedance to a second medium with a second acoustic impedance, the greater the difference between the impedances of both media, the less the energy transfer and the greater the reflection of the wave. For this reason, it is mentioned again that the device was designed to exhibit maximum acoustic coupling to the patient's tissue and maximum inherent rejection of environmental noise. In this way, the sound that is conducted from the point of support on the skin of the auscultated person is transmitted with a maximum coupling and those sounds (external noises) that travel through the air find a maximum rejection by traveling through a medium of different acoustic impedance like air, due to the noticeable differences in density and acoustic impedance (water 1,694,000 Ry versus 416.5 Ry, a ratio of more than 4000).

As already explained, the entire acoustic path from the outer membrane 1*a* to the lower spherical central member 1*b*, the acoustic coupler 3 and the sensor sheet 4 form a continuous state coupling solid whose acoustic impedance is similar to that of human tissue, thus allowing maximum coupling from the patient's skin to the sensor with Piezo PDVF sensor sheet 4 (polyvinylidene fluoride). This feature of the invention provides the maximum intracorporeal sound signal whose acoustic impedance is approximately 1,694,000 Ry as well as the rejection of external airborne sounds whose acoustic impedance is approximately 416.5 Ry In the device, the sensor sheet 4 is in turn connected to an electronic preamplifier 19 on the printed circuit board PCB 16 and which has an optimal input electrical impedance for the highest energy transfer of more than 10 MOhm, thus providing the maximum amplification of the electrical signal.

Figure 3A:
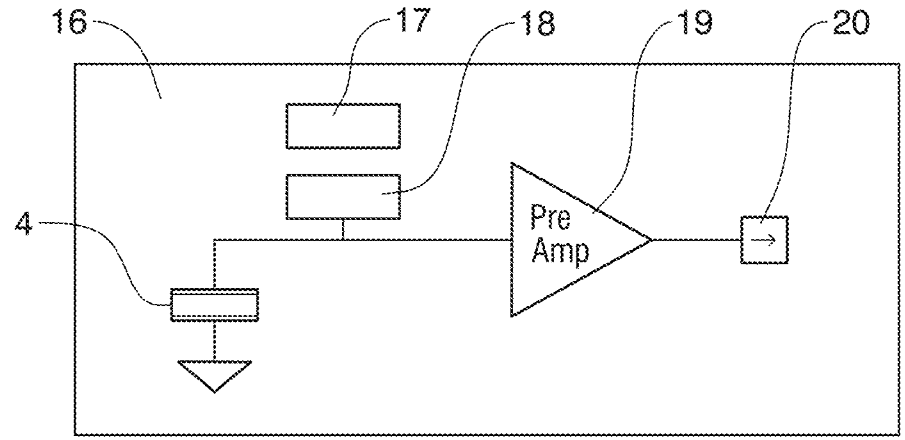
FIGS. 3A and 3B show the circuit block diagrams of the solid-state stethoscope for optimal body sound pickup with ambient noise rejection.
Figure 3B:
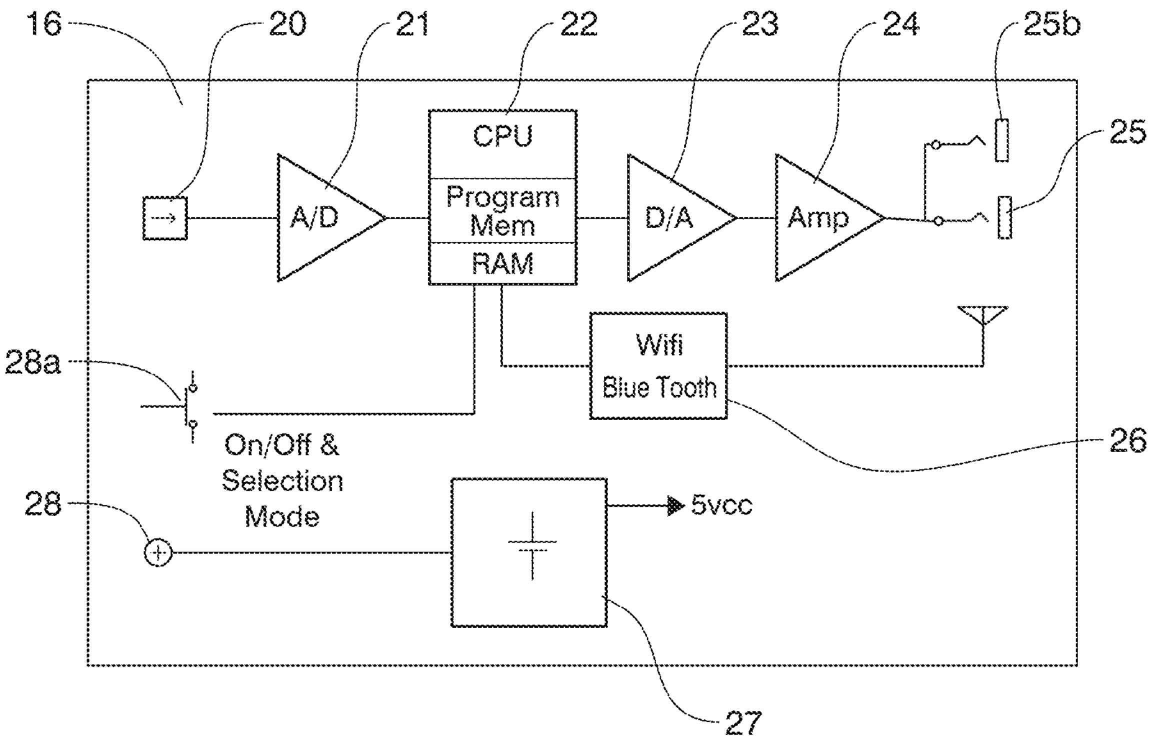

FIGS. 3A and 3B show that in the printed circuit board PCB 16 the main central PVDF sensor sheet 4 is connected to the very high input impedance preamplifier 19 (greater than 10 MOhm) which provides impedance matching, and drives the analog/digital converter (A/D) 21 to supply the digital signal processor (DSP) 22. A bias circuit 17 generates bias for the sensor sheet 4 and for the preamplifier 19 input and a latching circuit 18 limits the amplitude of the input signal within the desired levels.

On the printed circuit board PCB 16, the MAIN OUTPUT signal 20 is connected to the A/D converter 21 where the signal is digitized and then digitally processed by the DSP 22 which controls the gain and filters for the Wide, Bell, Diaphragm, etc. modes. The DSP 22 controls a digital output for digital streaming over a WiFi/Bluetooth link 26 and further connects to a digital/analog (D/A) converter 23 whose analog output is connected to an audio output amplifier 24 for power two optional headphones connected locally through an audio output connector 25, and an additional one 25*b* so that two people can listen simultaneously for training or shared diagnosis.

The unit is powered by a battery management circuit 27 which controls the charging of a battery cell 28 and provides power to the circuit for continuous operation of 6 hours, before recharging. The unit operates without a cord connection to the power line for maximum operator and patient safety, and includes circuitry to disable battery operation if the charger is connected. A button 28*a* turns the unit on and off and selects the different membrane modes.

The DSP processor 22 of the invention also allows selecting the type of auscultated sound, as well as its autonomous in-person or remote use by transmitting the sound in digital format through TCP/UDP (Transmission Control Protocol/User Datagram Protocol) or other protocols, or as an accessory element for a device called "Remote Clinical Office" which is another invention by the same inventor. In addition to impedance matching and signal amplification, the sound signal is digitized and digitally processed to provide standalone, local and remote use, as well as gain and membrane type filtering selection.

Noise Canceling Solid State Electronic Stethoscope with Acoustic Impedance Matched and Active Noise Cancellation The second embodiment of the present invention comprises, in addition to what is described in the first embodiment, an additional array of sensors for the active cancellation of environmental noise and handling noises, such as friction, creaks and other noises produced during auscultation.

Figure 2:
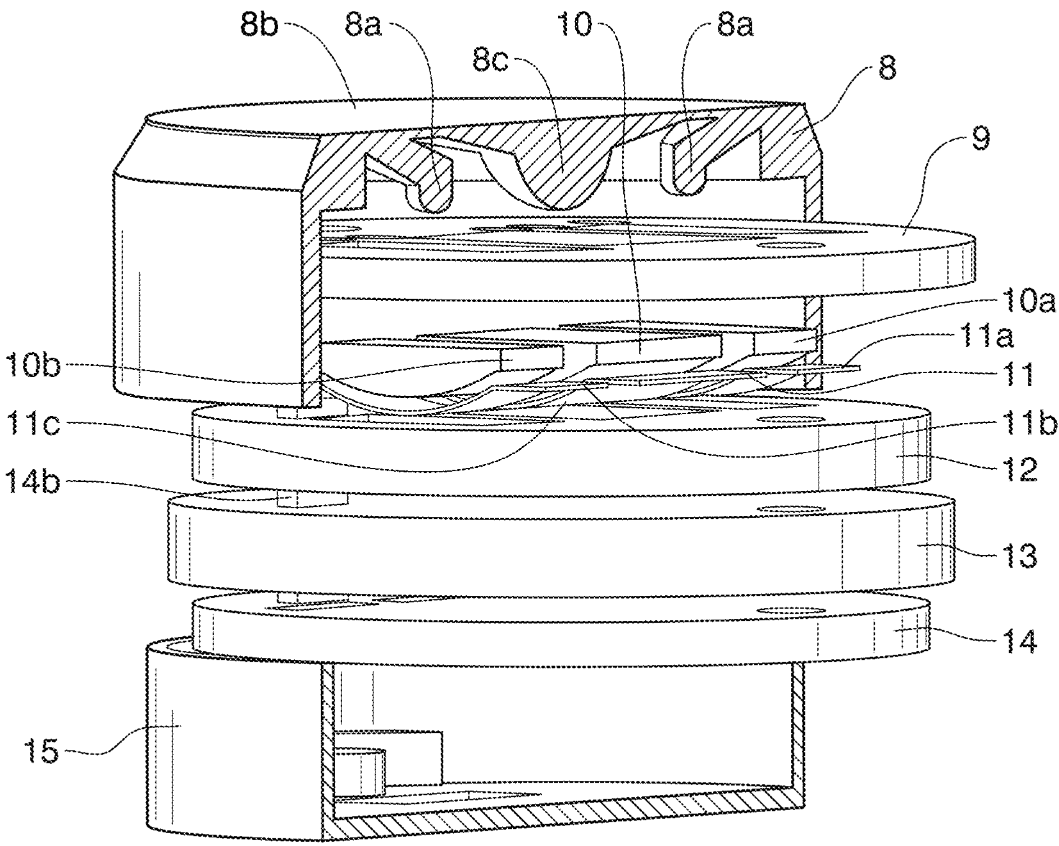
FIG. 2 shows an exploded view of the assembly and parts of the second embodiment of the stethoscope of the present invention.

FIG. 2 shows the second embodiment of the present invention comprising a solid-state direct-coupled electronic stethoscope based on an impedance-matched acoustic signal conduction mechanism to maximize the acquisition of sounds from the body with rejection of ambient noise and an additional array of sensors for active noise cancellation. In this way, the acoustic waves coming from the body of the auscultated patient are captured and transmitted with the greatest transfer of energy to the sensors, and the ambient noise signals that travel through the air are rejected due to the great impedance mismatch. Additionally, the additional sensors 11*a*, 11*b* mostly capture noise because they are placed in a lateral position closer to the possible sources of any remaining noise, mainly friction during use, for active cancellation by electronic subtractive cancellation.

FIG. 2 shows a cylindrical cap 8 with a membrane comprising an outer circular membrane 8*b* that rests on the patient's skin to auscultate sounds coming from the area of interest. This membrane, which in a preferred embodiment is 38 mm in diameter, has a conical interior volume terminated in a central spherical lower member 8*c* that is in contact with the central acoustic coupler 10 and two additional lateral spherical lower members 8*a* for receiving sounds from the lateral area of the cylindrical cap 8. The complete piece is preferably made of TPU (thermoplastic polyurethane) or silicone with similar characteristics, showing a density close to that of human tissue of 1.1 gr/cm3+−20%, that is, 0.88-1.32 gr/cm3. The material used for the cylindrical cap 8 with its membrane 8*b* is a biocompatible material that does not cause irritation when in contact with the skin, has great elasticity and mechanical resistance, is the first link in the acoustic signal acquisition path and has an impedance acoustics equivalent to that of human tissue. The diameter of 38 mm was chosen since it allows the best compromise of capturing acoustic vibrations versus comfort and accessibility to the various areas of the body to be auscultated. The outer membrane 8*b* of the cylindrical cap 8 has a thickness of 0.4 mm that provides resistance, as well as good coupling at low frequencies. The central acoustic coupler 10 is preferably 9 mm wide by 10 mm long, it is preferably made of flexible polyurethane (Ebalta® GM951) or any material with similar characteristics, implemented in a density close to that of human tissue of 1.1 gr/cm3+−20% that is, 0.88-1.32 gr/cm3. The central acoustic coupler 10 has a flat upper face in contact with the central spherical member 8*c* of the membrane 8*b*, receiving the acoustic vibrations coming from contact with the body auscultated by direct coupling, which also has a density similar to that of human soft tissue, and a curved lower face directly coupled directly by contact to the central sensor sheet 11, which is a piezoelectric sheet of Piezo PDVF (polyvinylidene fluoride or vinylidene polyfluoride), preferably 9 mm×17 mm and 45 μm thick, with silver micrometallic electrodes. The central sensor sheet 11 comprises a curved central area 11*c* with a maximum depth of 3 mm and flat lateral ends that converts the acoustic vibrations thus received into electrical impulses, thus obtaining maximum acoustic transfer and as a whole rejecting the noise coming from the air. The chosen curvature optimizes the propagation of acoustic waves on the central sensor sheet 11 in the direction of its longest longitudinal axis, thus transmitting the vibrations received on the axis in which the piezoelectric material of the central sensor sheet 11 Piezo PDVF has the greatest piezoelectric conversion efficiency.

In the same way, the additional lateral spherical lower members 8*a* are coupled by resting on the additional lateral acoustic couplers 10*a* and 10*b*. These additional lateral acoustic couplers 10*a* and 10*b* are made of the same material as the central acoustic coupler 10 and have half of its width. These additional lateral acoustic couplers 10*a* and 10*b*, in turn, are coupled by contacting the additional lateral sensor sheets 11*a* and 11*b* which are connected in electrical parallel mode. The additional lateral sensor sheets 11*a* and 11*b* are also made of Piezo PDVF (polyvinylidene fluoride or vinylidene polyfluoride), preferably 4.5 mm×17 mm and 45 μm thick, with silver micrometallic electrodes. In this way, since both lateral sensor sheets 11*a* and 11*b* show half the width of the central sensor sheet 11, a signal of similar magnitude of the one generated by the central sensor 11 is obtained.

The lateral acoustic couplers 10*a* and 10*b* are designed to have an acoustic impedance similar to that of human tissue, thus conducting vibrations to the central sensor sheet 11 and to the lateral sensor sheets 11*a* and 11*b* with maximum signal intensity and free of standing waves. Furthermore, this second embodiment additionally comprises an active noise cancellation device, formed by the group of 2 lateral sensor sheets 11*a* and 11*b* preferably manufactured with Piezo PDVF sensor sheets that act as 2 signal capture sectors, separate of the central sensor sheet 11.

The additional lateral sensor sheets 11*a* and 11*b* are strategically located to be equivalent in surface area and load capacity, to generate signals with the same sensitivity as the central sensor sheet 11. The rear plate 12 acts as a support (backing) for the set of lateral sensor sheets 11, 11*a* and 11*b* and for the acoustic couplers 10, 10*a* and 10*b*. The cylindrical backrest 13 contains a mass of preferably 16 g of copper. The rear plate 12 and the cylindrical backrest 13 are preferably constructed of ABS material or any material with similar characteristics, showing a density close to that of human tissue, of 1.1 gr/cm3+−20%, that is, 0.88-1.32 gr/cm3. The cylindrical backrest 13 provides additional support (inertial support mass) to the assembly (backing) to achieve good response at low frequencies of the auscultated sounds, obtaining a bandwidth of about 20 Hz to 4 Khz that provides all the range necessary for diagnosis in any auscultation territory.

The upper inner conductive cover 9 is preferably made of flexible silicone with high electrical conductivity and provides ground connection (GND) to the upper face (pole) of the Piezo PDVF lateral sensor sheets 11, 11*a* and 11*b*, both of which also act as shielding against electronic noise and mainly to the 50/60 hz electromagnetic noise coming from the urban electrical power lines. The vertical conductive connectors 14*b*, also preferably constructed of flexible silicone with high electrical conductivity, provide electrical connection to the underside of the PDVF Piezo lateral sensor sheets 11, 11*a* and 11*b*, up to the input contact pad (not shown) of the printed circuit board PCB 14. Lastly, the lower conductive cover 15, preferably made of flexible silicone with high electrical conductivity, encapsulates the entire assembly, completing the electromagnetic shielding with the upper inner conductive cover 9.

Figures 4A, 4B:
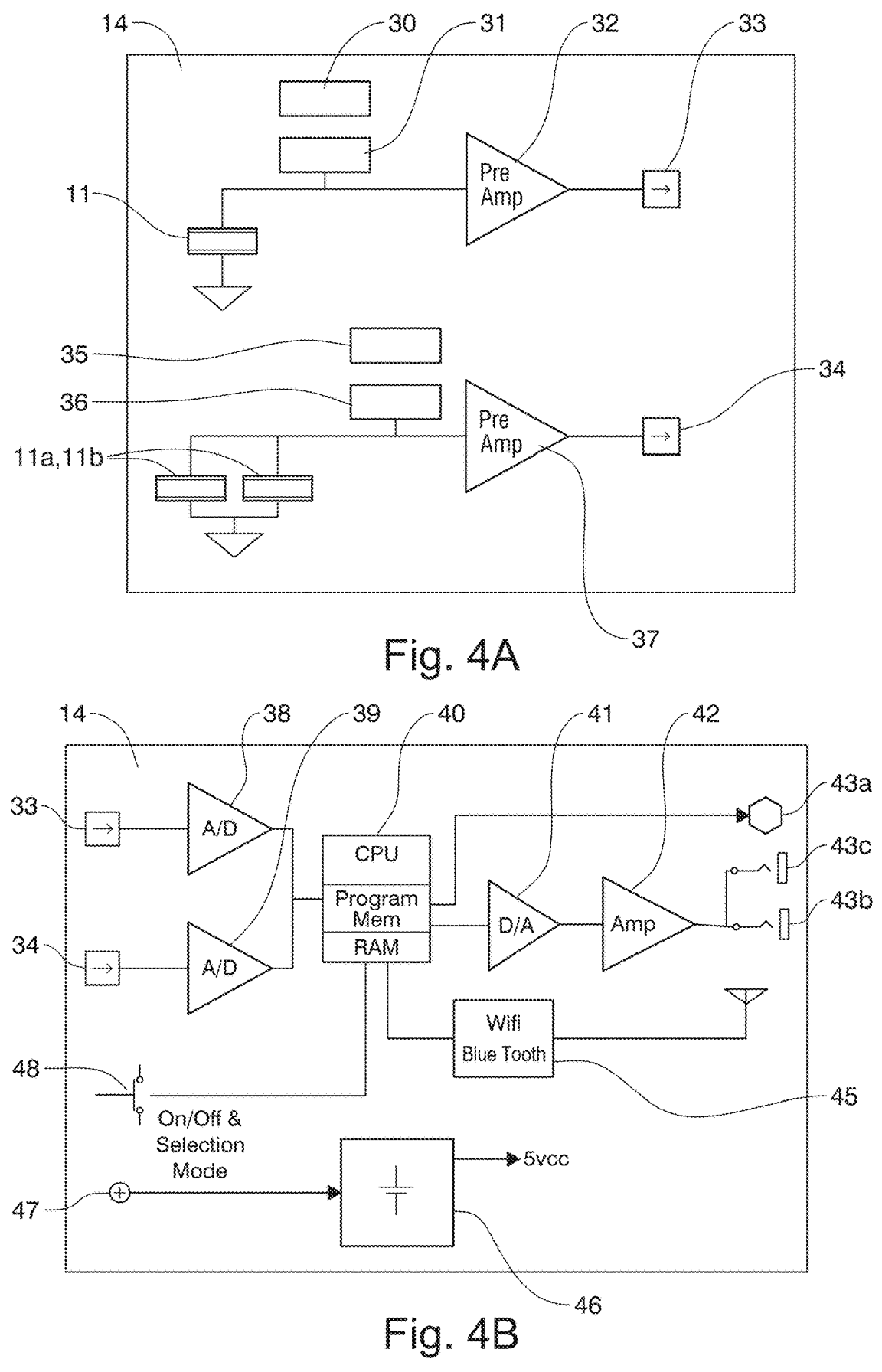

FIGS. 4A and 4B show that in the printed circuit board PCB 14 the Piezoelectric PVDF central sensor sheet 11 is connected to a first preamplifier 32 of very high input impedance (greater than 10 MOhm) that provides impedance matching and is necessary to drive a first differential A/D converter 38 of the DSP digital signal processor 40. A first bias circuit 30 generates bias for the central sensor sheet 11 and for the input of the high impedance preamplifier 32 and a first latching circuit 31 limits the input signal amplitude within the desired levels.

The lateral sensor sheets 11*a* and 11*b* are connected to each other to a second preamplifier 37 of very high input impedance (greater than 10 MOhm) that provides impedance matching and is necessary to drive the second differential A/D converter 39 of the DSP 40. A second bias circuit 35 generates bias for each lateral sensor sheet 11*a* and 11*b* and for the input of the second high impedance preamplifier 37 and a second latching circuit 36 limits the amplitude of the input signal within the desired levels.

The output signal 33 of the preamplifier 32 is connected to the first A/D converter 38 and each of the output signals 34 of the lateral sensor sheets 11*a* and 11*b* are connected to the second A/D converter 39. The signals are digitally processed and subtracted by the DSP 40 which controls the gain and filters for the Wide, Bell and Aperture modes and the NR noise reduction modes. The DSP 40 features a direct digital output 43*a* and further controls a digital output for digital streaming over a WiFi link 45 and a digital/analog D/A converter 41 and an audio output amplifier 42 for optional locally connected headphones (not shown) through an output connector 43*b* and another additional connector 43*c* so that two people can listen simultaneously for training or shared diagnosis.

The unit is powered by a battery management circuit 46 which controls the charging of a battery cell 47 and provides power to the circuit for continuous operation of 6 hours, before recharging. The unit operates without wire connections to the power line for maximum operator and patient safety and includes circuitry to disable battery operation if the charger is connected. A push button 48 is used to turn the unit on and off and select the different membrane modes.

The central sensor sheet 11 receives all sounds, that is, the signals that the user wishes to listen to, as well as residual ambient noise. At the same time, the two lateral sensors sheets 11*a* and 11*b* receive almost only the residual ambient noise and noise content from the mechanical transmission of the housing assembly and/or from the movements and friction of the user. In the electronic circuit, the amplified signal from the central sensor sheet 11 is then added to the signal from both lateral sensor sheets 11*a* and 11*b* whose polarity is first reversed to obtain a differential acoustic signal. In this way the signal from the lateral sensor sheets 11*a* and 11*b* is effectively subtracted from the total signal obtained in the central sensor sheet 11, thus canceling the noise signals, and leaving only the desired ones coming from the central area. This arrangement achieves additional high rejection of environmental noise, friction and any noise generated by normal handling when using a stethoscope, obtaining a clear and noise-free signal.

The upper inner conductive cover 9, made of flexible silicone with high electrical conductivity, provides connection to the electrical ground (GND) of the device to act as a shield against possible external electrical noises (50/60 Hz and others) and to shield the inner part of the electronic circuits that carry out the amplification and cancellation of noise by subtraction between the signal from the central sensor sheet 11 and those from the lateral sensor sheets 11*a* and 11*b*. The electronic circuitry provides, in turn, electrical impedance matching, noise cancellation, electrical noise filtering, signal processing and headphone output or a data transmission module for remote monitoring.

In this way, the solid-state electronic stethoscope of the present invention optimizes the quality of auscultation in patients through 3 new features:

1. Optimal adapting of the acoustic impedance from the patient's skin to the sensors using polyvinylidene fluoride sheets and acoustic adapters;
2. Simultaneous capture of noises not related to auscultation;
3. Electronic noise cancellation processing by subtraction of electronic signals and processing of the signal obtained, to separate the obtained sounds from the noise.

As already explained, the stethoscope of the present invention comprises filters of the Wide, Bell, Diaphragm, etc. type, which are capable of producing sounds similar to those of a conventional stethoscope in order to replace it, taking advantage of the training of the doctors who perform auscultation with the benefit of being able to control gain, filters and being able to selectively listen at a much higher volume.

Based on the advantages obtained by the stethoscope of the present invention, a patient can be examined using current training and experience either locally or remotely from a healthcare provider with the described advantages.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. A solid state stethoscope, comprising an outer membrane (1*a*) for contacting the skin of a patient, an upper inner conductive cover (7*b*) located below said outer membrane (1*a*), a lower conductive cover (2), an acoustic coupler (3), a sensor sheet (4), a rear plate (5) located below the sensor sheet (4) and resting on a cylindrical backrest (6), a printed circuit board PCB (16) located under said cylindrical backrest (6), wherein said outer membrane (1*a*) is made of TPU (thermoplastic polyurethane) or silicone and comprises a lower spherical central member (1*b*), said sheet sensor (4) is made of Piezo PVDF (polyvinylidene fluoride or vinylidene polyfluoride) with silver micrometallic electrodes and has a rectangular perimeter shape with a curved central zone (4*a*) and flat sides, and wherein the stethoscope comprises the acoustic coupler (3), the acoustic coupler (3) being made of flexible polyurethane and having a flat upper face (3*a*) in contact with the lower spherical central member (1*b*) and a curved lower face (3*b*) resting on the sensor sheet (4), wherein a path of an acoustic signal formed by said outer membrane (1*a*), said lower spherical central member (1*b*), said acoustic coupler (3) and said sensor sheet (4) has an acoustic impedance similar to that of the skin of said patient, thus being capable of generating an acoustic impedance adaptation between said skin and said sensor sheet (4), achieving optimal sensitivity and maximum rejection of environmental noise.

2. The solid state stethoscope according to claim 1, wherein said rear plate (5) and said cylindrical backrest (6) are made of ABS, and wherein said outer membrane (1*a*), said acoustic coupler (3), said rear plate (5) and said cylindrical backrest (6) all have a density of 0.88-1.32 gr/cm3, that is, similar to that of human soft tissue.

3. The solid state stethoscope according to claim 1, wherein said rear plate (5) and said cylindrical backrest (6) are electrical insulators of the printed circuit board PCB (16) and provide ground connection.

4. The solid state stethoscope according to claim 1, wherein said printed circuit board PCB (16) comprises a bias circuit (17) for the sensor sheet (4) and for the input of a preamplifier (19) of very high input impedance, and comprises a latching circuit (18).

5. The solid state stethoscope according to claim 4, wherein the output of said high input impedance preamplifier (19) is connected to an analog/digital A/D converter (21), which in turn connects to a digital signal processor DSP (22), both comprised in said printed circuit board PCB (16).

6. The solid state stethoscope according to claim 5, wherein the input impedance of the signal preamplifier (19) is greater than 10 MOhm.

7. The solid state stethoscope according to claim 5, wherein said digital signal processor DSP (22) emits a signal output for digital transmission through a WiFi and Bluetooth link (26) and also connects to a digital/analog converter D/A (23) whose analog output is connected to an audio output amplifier (24) to supply said signal output to headphones through audio output connectors (25 and 25*b*).

8. The solid state stethoscope according to claim 7, wherein the digital signal processor DSP (22) allows selecting the type of sound heard, as well as selecting between local or remote use and transmits the sound in digital format using TCP/UDP (Transmission Control Protocol/User Datagram Protocol).

9. The solid state stethoscope according to claim 5, further comprising a battery management circuit (27) and a battery cell (28) and a button (28*a*) for turning on, turning off and selecting the different membrane Wide, Bell, or Diaphragm modes.

10. A solid state stethoscope, comprising an outer membrane (8*b*) in a central area of a cylindrical cap (8) for contacting the skin of a patient, an upper inner conductive cover (9) located below said outer r membrane (8*b*), a lower conductive cover (15), a central sensor sheet (11) for capturing auscultated signal and two lateral sensor sheets (11*a*, 11*b*) for capturing unwanted noise, a rear plate (12) located below the two lateral sensor sheets (11*a*, 11*b*) and resting on a cylindrical backrest (13), a printed circuit board PCB (14) comprising electronic circuits located below said cylindrical backrest (13), wherein said outer membrane (8*b*) is made of TPU (thermoplastic polyurethane) or silicone and comprises a central spherical lower member (8*c*), said central sensor sheet (11) and said lateral sensor sheets (11*a*, 11*b*) each have a rectangular perimeter shape with a curved central area (11*c*) and flat sides, and wherein the stethoscope also comprises a central acoustic coupler (10) placed on said central sensor sheet (11) and in close contact therewith, and also comprises two lateral acoustic couplers (10*a*, 10*b*) each placed on a corresponding lateral sensor sheet (11*a*, 11*b*), in close contact therewith and fixed by said upper inner conductive cover (9), and wherein the central acoustic coupler (10) and the lateral acoustic couplers (10*a*, 10*b*) are made of flexible polyurethane and each have a flat upper face, and wherein the flat upper face of the central acoustic coupler (10) is in contact with the central spherical lower member (8*c*) of the outer membrane (8*b*), and the flat upper face of each of the lateral acoustic couplers (10*a*, 10*b*) is in contact with a corresponding lateral spherical lower member (8*a*) of a lateral area of the cylindrical cap (8), and wherein the central acoustic coupler (10) has a curved lower face resting on the central sensor sheet (11) and each of the lateral acoustic couplers (10*a*, 10*b*) has a curved lower face resting on a corresponding lateral sensor sheet (11*a*, 11*b*), where said central sensor sheet (11) and said lateral sensor sheets (11*a*, 11*b*) are made of Piezo PVDF (polyvinylidene fluoride or vinylidene polyfluoride) with silver micrometallic electrodes, whereby a path of an acoustic signal formed by said outer membrane (8*b*), said central spherical lower members (8*c*), said central acoustic coupler (10) and said central sensor sheet (11), and the path of the acoustic signal formed by said outer membrane (8*b*), said lateral spherical lower members (8*a*), said lateral acoustic couplers (10, 10*b*) and said lateral sensor sheets (11*a*, 11*b*), have an acoustic impedance similar to that of the skin of said patient, thus capable of generating an acoustic impedance adaptation between said skin and said central sensor sheet (11) and an acoustic impedance match between said skin and said lateral sensor sheets (11*a*, 11*b*); and wherein, in the electronic circuits an amplified signal from the central sensor (11) is added to an inverted polarity signal from both lateral sensor sheets (11*a*, 11*b*) to obtain a differential acoustic signal, by which the stethoscope is capable of canceling unwanted noise signals captured by said lateral sensors (11*a*, 11*b*) and leaving only desired signals coming from an auscultated area taken by the central sensor sheet (11).

11. The solid state stethoscope according to claim 10, wherein said rear plate (12) and said cylindrical backrest (13) are made of ABS (Acrylonitrile Butadiene Styrene), and wherein the outer membrane (8*b*), the central acoustic coupler (10), the lateral acoustic couplers (10*a*, 10*b*), said central sensor sheet (11) and said lateral sensor sheets (11*a*, 11*b*) all have a density of 1.1 gr/cm3+/−20%, that is, similar to that of human soft tissue.

12. The solid state stethoscope according to claim 10, wherein the unwanted noise comprises residual ambient noise and noise from the mechanical transmission of at least one of the housing assembly or from the movements and friction of the user.

13. The solid state stethoscope according to claim 10, wherein said rear plate (12) and said cylindrical backrest (13) are electrical insulators of the printed circuit board PCB (14) and provide a grounding connection.

14. The solid state stethoscope according to claim 10, wherein said electronic circuits comprise a first bias circuit (30) and a first latching circuit (31) capable of limiting the amplitude of the input signal within the desired levels for the input of a first preamplifier (32) of very high impedance of the signal coming from the central sensor sheet (11); a second bias circuit (35) and a second latching circuit (36) capable of limiting the amplitude of the input signal within the desired levels for the input of a second preamplifier (37) of very high impedance each of the signals coming from the lateral sensor sheets (11*a*, 11*b*).

15. The solid state stethoscope according to claim 14, wherein the output of said first very high impedance preamplifier (32) is connected to a first analog/digital A/D converter (38) and which in turn is connected to a digital signal processor DSP (40); and the output of said second very high impedance preamplifier (37) is connected to an analog/digital (A/D) converter (39) and which in turn is connected to said digital signal processor DSP (40).

16. The solid state stethoscope according to claim 15, wherein the signal processor DSP (40) allows selecting the type of sound auscultated, as well as selecting between local or remote use and transmits the sound in digital format through TCP/UDP (Transmission Control Protocol/User Datagram Protocol).

17. The solid state stethoscope according to claim 14, wherein the input impedance of the first and second signal preamplifiers (32, 37) is greater than 10 MOhm.

18. The solid state stethoscope according to claim 14, wherein said digital signal processor DSP (40) controls a digital output for digital transmission over a WiFi and Bluetooth link (45) and further connects to a digital/analog converter D/A (41) having an analog output is connected to an audio output amplifier (42) to power headphones through audio output connectors (43*b* and 43*c*).

19. The solid state stethoscope according to claim 14, further comprising a battery management circuit (46) and a battery cell (47) and a push button (48) for on, off and selection of the different membrane Wide, Bell, or Diaphragm modes.

20. The solid state stethoscope according to claim 10, wherein the central sensor sheet (11) and the lateral sensor sheets (11*a*, 11*b*) have front electrodes that are connected to the electrical ground of the stethoscope.

* * * * *